US012601730B2

(12) United States Patent
Li et al.

(10) Patent No.: US 12,601,730 B2
(45) Date of Patent: Apr. 14, 2026

(54) METHOD FOR ASSESSING NITROGEN LEACHING RISK BASED ON FARMLAND SOIL PRESSURE

(71) Applicants: Institute of Environmental Protection Research and Monitoring, Ministry of Agriculture and Rural Affairs, Tianjin (CN); Institute of Agricultural Resources and Regional Planning, Chinese Academy of Agricultural Sciences, Beijing (CN)

(72) Inventors: Jie Li, Tianjin (CN); Guilong Zhang, Tianjin (CN); Yan Xu, Tianjin (CN); Lili Wang, Tianjin (CN); Xinxiu Wang, Beijing (CN); Houyu Li, Tianjin (CN); Yungui Zhang, Beijing (CN); Jianning Zhao, Tianjin (CN)

( * ) Notice: Subject to any disclaimer, the term of this patent is extended or adjusted under 35 U.S.C. 154(b) by 0 days.

(21) Appl. No.: 18/923,060

(22) Filed: Oct. 22, 2024

(65) Prior Publication Data

US 2026/0009781 A1     Jan. 8, 2026

(30) Foreign Application Priority Data

Jul. 2, 2024    (CN) .......................... 202410875020.7

(51) Int. Cl.
| | |
|---|---|
| *G01N 33/24* | (2006.01) |
| *E02D 1/00* | (2006.01) |
| *G01V 11/00* | (2006.01) |
| *G06F 30/20* | (2020.01) |
| *G06Q 10/04* | (2023.01) |

(52) U.S. Cl.
CPC ................................ *G01N 33/245* (2024.05)

(58) Field of Classification Search
CPC ...... G01N 33/245; G01N 33/24; G06Q 10/04; E02D 1/00; G01V 11/10; G06F 30/20
USPC ............................................................ 702/9
See application file for complete search history.

(56) References Cited

U.S. PATENT DOCUMENTS

| | | | |
|---|---|---|---|
| 2021/0300836 A1* | 9/2021 | Li | ........................... C05F 17/60 |
| 2024/0125756 A1* | 4/2024 | Zink | .................... C12Q 1/6888 |
| 2024/0426801 A1* | 12/2024 | Li | ........................ G01N 1/4055 |

FOREIGN PATENT DOCUMENTS

| | | |
|---|---|---|
| CN | 113919569 A | 1/2022 |
| CN | 115754245 A | 3/2023 |
| CN | 116680972 A | 9/2023 |

* cited by examiner

*Primary Examiner* — Michael P Nghiem

(57) ABSTRACT

Disclosed is a method for assessing nitrogen leaching risk based on farmland soil pressure, including the following steps: acquiring soil drilling pressure data from a plurality of soil layers of different depths on soil to be tested using a soil drilling device, to obtain raw soil drilling pressure data; comparing a calibration curve with a raw soil drilling pressure curve; setting an interquartile range (IQR) coefficient based on a first fluctuation factor and a second fluctuation factor, and constructing a box plot of the raw soil drilling pressure data based on the IQR coefficient; and determining a peak soil drilling pressure according to the box plot of the raw soil drilling pressure data, and determining nitrogen leaching risk according to a depth interval of soil layer. The box plot is utilized to filter out abnormal values, ensuring the accuracy of assessing the nitrogen leaching risk in soil.

7 Claims, 2 Drawing Sheets

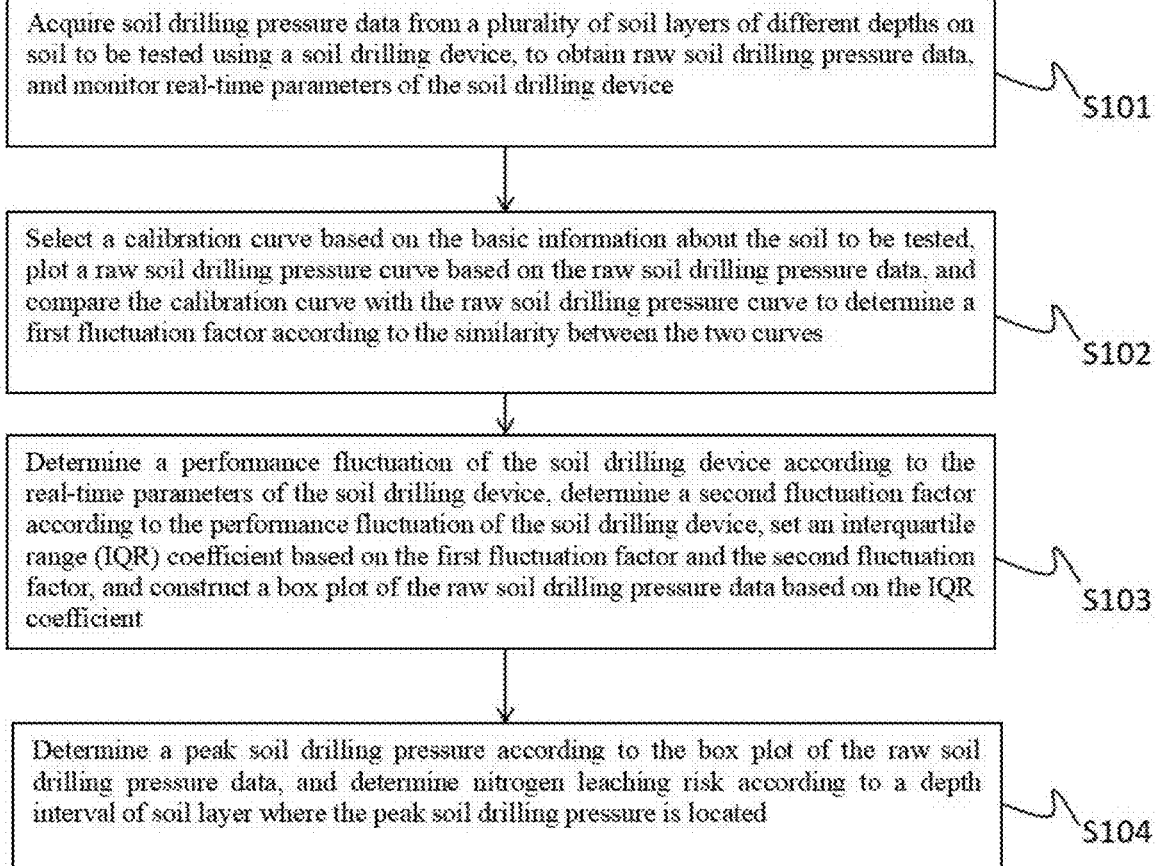

Acquire soil drilling pressure data from a plurality of soil layers of different depths on soil to be tested using a soil drilling device, to obtain raw soil drilling pressure data, and monitor real-time parameters of the soil drilling device ⟶ S101

Select a calibration curve based on the basic information about the soil to be tested, plot a raw soil drilling pressure curve based on the raw soil drilling pressure data, and compare the calibration curve with the raw soil drilling pressure curve to determine a first fluctuation factor according to the similarity between the two curves ⟶ S102

Determine a performance fluctuation of the soil drilling device according to the real-time parameters of the soil drilling device, determine a second fluctuation factor according to the performance fluctuation of the soil drilling device, set an interquartile range (IQR) coefficient based on the first fluctuation factor and the second fluctuation factor, and construct a box plot of the raw soil drilling pressure data based on the IQR coefficient ⟶ S103

Determine a peak soil drilling pressure according to the box plot of the raw soil drilling pressure data, and determine nitrogen leaching risk according to a depth interval of soil layer where the peak soil drilling pressure is located ⟶ S104

FIG. 1

METHOD FOR ASSESSING NITROGEN LEACHING RISK BASED ON FARMLAND SOIL PRESSURE

CROSS-REFERENCE TO RELATED APPLICATION

This application claims priority of Chinese Patent Application No. 202410875020.7, filed on Jul. 2, 2024, the entire contents of which are incorporated herein by reference.

TECHNICAL FIELD

The present application relates to the technical field of specific data processing, and more specifically relates to a method for assessing nitrogen leaching risk based on farmland soil pressure.

BACKGROUND

In modern agricultural production, particularly in facility agriculture, a highly intensive management mode of "excessive fertilization and irrigation" is often employed for high yields, and excessive nitrogen is prone to leaching downward due to precipitation or irrigation, seriously threatening the ecological safety of water bodies in a basin. Monitoring results of groundwater quality from 2013 to 2017 indicate that three kinds of nitrogen (ammonia nitrogen, nitrite nitrogen, and nitrate nitrogen) significantly exceed the limit, and nitrogen leaching loss has been an agricultural non-point source pollution problem that needs to be taken seriously.

Current monitoring methods for nitrogen leaching include in-situ measurement and model fitting. In-situ measurement mainly includes a leaching barrel method, a ceramic cup method, and a lysimeter method, all of which are time-consuming and labor-intensive, requiring sampling for testing. Model fitting methods include denitrification-decomposition (DNDC), nitrogen leaching and economic analysis package (NLEAP), leaching estimation and chemistry model (LEACHM), decision support system for agrotechnology transfer (DSSAT), root zone water quality model (RZWQM), Hydrus-1D, and soil and water assessment tool (SWAT), all of which require substantial monitoring data, have high use requirements and applicability problems. Accordingly, there is an urgent need to develop simple assessment methods to accurately determine the in-situ nitrogen leaching risk in soil.

For the model fitting methods in the prior art, except for requiring substantial data and having high use requirements, the performance difference in device and different soil conditions can affect the accuracy of the directly collected pressure data, resulting in a significant number of abnormal values in the collected pressure data, and poor adaptability in data processing. The presence of abnormal values can affect the determination of peak pressure, reducing the accuracy and precision of assessing the nitrogen leaching risk in soil.

Therefore, improving the adaptability of data processing and the accuracy of assessing the nitrogen leaching risk in soil is a technical problem that needs to be addressed currently.

SUMMARY

The present disclosure provides a method for assessing nitrogen leaching risk based on farmland soil pressure to solve the technical problems of low adaptability of data processing and poor accuracy of assessing nitrogen leaching risk of soil in the prior art. The method includes:

acquiring soil drilling pressure data from a plurality of soil layers of different depths on soil to be tested using a soil drilling device, to obtain raw soil drilling pressure data, and monitoring real-time parameters of the soil drilling device;

selecting a calibration curve based on the basic information about the soil to be tested, plotting a raw soil drilling pressure curve based on the raw soil drilling pressure data, and comparing the calibration curve with the raw soil drilling pressure curve to determine a first fluctuation factor according to the similarity between the two curves;

determining a performance fluctuation of the soil drilling device according to the real-time parameters of the soil drilling device, determining a second fluctuation factor according to the performance fluctuation of the soil drilling device, setting an interquartile range (IQR) coefficient based on the first fluctuation factor and the second fluctuation factor, and constructing a box plot of the raw soil drilling pressure data based on the IQR coefficient; and determining a peak soil drilling pressure according to the box plot of the raw soil drilling pressure data, and determining nitrogen leaching risk according to a depth interval of soil layer where the peak soil drilling pressure is located.

In some embodiments of the present application, the selecting a calibration curve based on the basic information about the soil to be tested includes:

the basic information of the soil to be tested including humidity, density, and compactness, setting a composite index according to the humidity, the density, and the compactness, and storing preset calibration curves corresponding to different composite indexes and soil drilling pressure in a database, the calibration curve representing a range of the soil drilling pressure varying with soil depth; and identifying, according to an actual composite index of the soil to be tested, a calibration curve corresponding to the same composite index in the database.

In some embodiments of the present application, the comparing the calibration curve with the raw soil drilling pressure curve to determine a first fluctuation factor according to the similarity between the two curves includes:

the similarity between the two curves being 100%, and the first fluctuation factor being 0 in a case that the raw soil drilling pressure curve is entirely within a range of the calibration curve; and otherwise, splitting a portion of the raw soil drilling pressure curve that exceeds the range of the calibration curve into a plurality of exceedance curves according to the soil layer depth, calculating an average difference between each of the exceedance curves and a boundary of the calibration curve, integrating all average differences to determine the similarity, and mapping one first fluctuation factor through the similarity.

In some embodiments of the present application, the determining a performance fluctuation of the soil drilling device according to the real-time parameters of the soil drilling device includes:

obtaining the real-time parameters of the soil drilling device during soil drilling, constructing a parameter change curve for each of the real-time parameters changing over time, splitting each parameter change curve into a plurality of small curves according to the fluctuation degree of each of the real-time parameters, calculating a slope change of each of the small curves, to obtain an average value of overall slope change of the parameter change curve, dividing the real-time parameters into stable parameters and unstable parameters according to the average value of slope change, and performing standardization processing on the stable parameters and the unstable parameters; and determining the performance fluctuation of the soil drilling device according to the stable parameters and the unstable parameters;

$$M = \sum_{i=1}^{n1} (\alpha_i Q_i) \ln \left\{ \frac{\sum_{j=0}^{n2} (\beta_j W_j)}{k_1} \right\} - M_0$$

where M represents the performance fluctuation of the soil drilling device, n1 represents the number of types of the stable parameters, $\alpha_i$ represents a performance weight of an $i_{th}$ type of stable parameters, $Q_i$ represents a size of the $i_{th}$ type of stable parameters, n2 represents the number of types of the unstable parameters, $\beta_j$ represents a performance weight of a $j_{th}$ type of unstable parameters, $W_j$ represents a size of the $j_{th}$ type of unstable parameters, $k_1$ represents a first constant, and $M_0$ represents a standard performance fluctuation range of the soil drilling device.

In some embodiments of the present application, the setting an IQR coefficient based on the first fluctuation factor and the second fluctuation factor, and constructing a box plot of the raw soil drilling pressure data based on the IQR coefficient includes:

$$D = \left[ \left( \gamma_1 \max\{s_1, s_2\} + \gamma_2 \left( \frac{s_1 + s_2}{2} \right) \right) \rightarrow D_1 \right] + D_2$$

where D represents the IQR coefficient, $\gamma_1$ represents a fluctuation weight of a larger fluctuation factor, $\max\{s_1, s_2\}$ is a larger one in the first fluctuation factor and the second fluctuation factor, $s_1$ represents the first fluctuation factor, $s_2$ represents the second fluctuation factor, $\gamma_2$ represents a fluctuation weight of an average value of the first fluctuation factor and the second fluctuation factor, $$\left( \gamma_1 \max\{s_1, s_2\} + \gamma_2 \left( \frac{s_1 + s_2}{2} \right) \right) \rightarrow D_1$$

represents an IQR compensation coefficient obtained by jointly mapping the larger fluctuation factor and the average value of the fluctuation factors, and $D_2$ represents an initial IQR coefficient; and determining upper and lower bounds in the box plot according to the IQR coefficient, from which the box plot of the raw soil drilling pressure data is constructed.

In some embodiments of the present application, the determining a peak soil drilling pressure according to the box plot of the raw soil drilling pressure data includes: differentiating normal soil drilling pressure data from abnormal soil drilling pressure data according to the upper and lower bounds in the box plot of the raw soil drilling pressure data, determining the peak soil drilling pressure in the normal soil drilling pressure data, and removing the abnormal soil drilling pressure data.

In some embodiments of the present application, the determining nitrogen leaching risk according to a depth interval of soil layer where the peak soil drilling pressure is located includes: obtaining other soil conditions, including groundwater underflow and soil barriers, and comprehensively determining the nitrogen leaching risk by combining the groundwater underflow, the soil barriers, and the depth interval of soil layer.

Accordingly, the present application also provides a system for assessing nitrogen leaching risk in farmland, including:

a soil drilling module, configured to acquire soil drilling pressure data from a plurality of soil layers of different depths on soil to be tested using a soil drilling device, to obtain raw soil drilling pressure data, and monitor real-time parameters of the soil drilling device;

a calibration module, configured to select a calibration curve based on the basic information about the soil to be tested, plot a raw soil drilling pressure curve based on the raw soil drilling pressure data, and compare the calibration curve with the raw soil drilling pressure curve to determine a first fluctuation factor according to the similarity between the two curves;

a construction module, configured to determine a performance fluctuation of the soil drilling device according to the real-time parameters of the soil drilling device, determine a second fluctuation factor according to the performance fluctuation of the soil drilling device, set an IQR coefficient based on the first fluctuation factor and the second fluctuation factor, and construct a box plot of the raw soil drilling pressure data based on the IQR coefficient; and an assessment module, configured to determine a peak soil drilling pressure according to the box plot of the raw soil drilling pressure data, and determine nitrogen leaching risk according to a depth interval of soil layer where the peak soil drilling pressure is located.

According to the above technical solutions, soil drilling pressure data is acquired from a plurality of soil layers of different depths on soil to be tested using a soil drilling device, to obtain raw soil drilling pressure data, and real-time parameters of the soil drilling device are monitored; a calibration curve is selected based on the basic information about the soil to be tested, a raw soil drilling pressure curve is plotted based on the raw soil drilling pressure data, and the calibration curve is compared with the raw soil drilling pressure curve to determine a first fluctuation factor according to the similarity between the two curves; a performance fluctuation of the soil drilling device is determined according to the real-time parameters of the soil drilling device, a second fluctuation factor is determined according to the performance fluctuation of the soil drilling device, an IQR coefficient is set based on the first fluctuation factor and the second fluctuation factor, and a box plot of the raw soil drilling pressure data is constructed based on the IQR coefficient; and a peak soil drilling pressure is determined according to the box plot of the raw soil drilling pressure data, and nitrogen leaching risk is determined according to a depth interval of soil layer where the peak soil drilling pressure is located.

Beneficial effects: in the present application, the IQR coefficient is set based on the first fluctuation factor and the second fluctuation factor; the impact of both the soil drilling device and soil conditions on data acquisition is comprehensively considered, and a reasonable IQR coefficient is set to construct the box plot of the pressure data, allowing for the filtering out of abnormal values. This improves the adaptability of data processing and accurately determines peak pressure, ensuring the accuracy of assessing the nitrogen leaching risk in soil.

BRIEF DESCRIPTION OF THE DRAWINGS

To state the technical solutions of the embodiments in the present application clearer, the attached drawings needed in the description of the embodiments are briefly introduced below. Obviously, the drawings described below are some embodiments in the present application, and for those ordinary skilled in the art, other drawings can be obtained according to these drawings without creative efforts.

FIG. 1 is a flow chart of a method for assessing nitrogen leaching risk based on farmland soil pressure according to an embodiment of the present disclosure.

DETAILED DESCRIPTION

Embodiment 1

Figure 2:
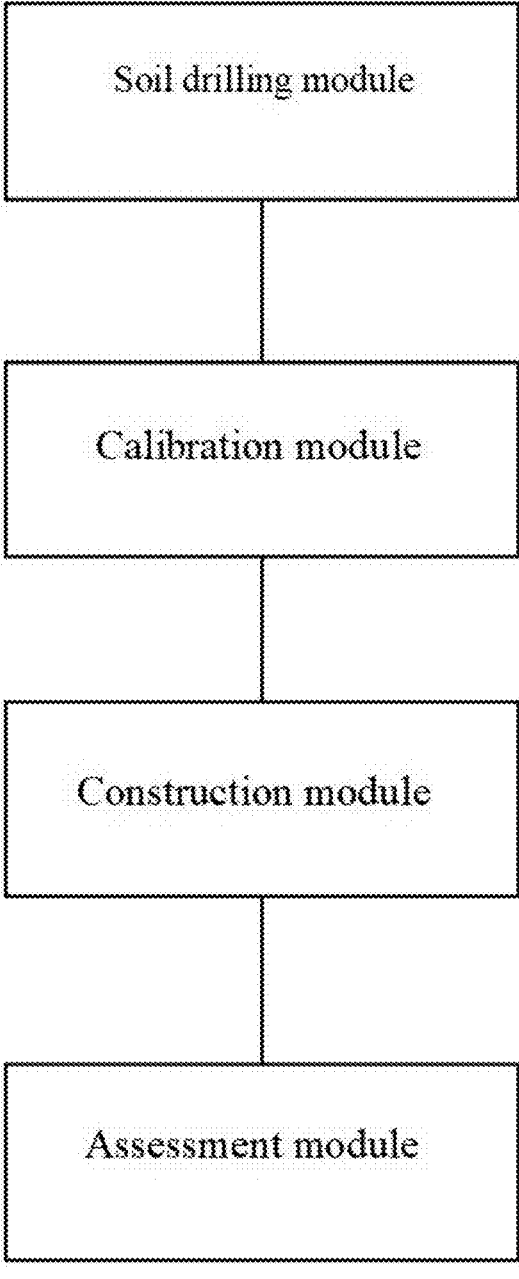
FIG. 2 is a schematic structural diagram of a system for assessing nitrogen leaching risk in farmland according to an embodiment of the present disclosure.

The technical solutions of the embodiments in the present application will be described clearly and completely by reference to the accompanying drawings of the embodiments in the present application below. Obviously, the embodiments described are only some, rather than all embodiments of the present application. On the basis of the embodiments of the present application, all other embodiments obtained by those ordinary skilled in the art without creative efforts fall within the scope of protection of the present application.

The embodiment of the present application provides a method for assessing nitrogen leaching risk based on farmland soil pressure. The mechanical composition of soil refers to the percentage of mineral particles at various levels in the soil, reflecting the size and quantity of mineral particles in the soil and significantly influencing the process of nitrogen leaching in the soil. The soil texture (sandy soil, loam, clay) can be determined based on the mechanical composition. Sandy soil has larger particles, numerous pores, and good water permeability, but has poor water retention capacity and relatively low nutrient content. Loam, a soil type between sandy soil and clay, has particles of different sizes and pores of moderate size, thus enabling good drainage and water retention, and serving as the soil most suitable for agricultural cultivation. Clay has extremely fine particles, resulting in poor air permeability and water permeability but strong water-holding and retention capabilities. Clay is sticky and becomes harder after drying, which is difficult to cultivate. The soil compactness follows the order of: clay>loam>sandy soil. Therefore, the soil texture can be determined according to the difficulty level (peak pressure) of sampling, and the nutrient retention status can be determined based on the soil texture, further assessing the risk of nitrogen leaching into the ground.

As shown in FIG. 1, the method includes the following steps.

Step S101, soil drilling pressure data is acquired from a plurality of soil layers of different depths on soil to be tested using a soil drilling device, to obtain raw soil drilling pressure data, and real-time parameters of the soil drilling device are monitored.

In this embodiment, an electric soil drill is driven by a motor, with a higher efficiency, and is suitable for survey in a medium area; and a hydraulic soil drill is driven by hydraulic power, with a higher efficiency, and is suitable for survey and sampling in a large area. A sensor is mounted on the soil drilling device to acquire the soil drilling pressure data.

Step S102, a calibration curve is selected based on the basic information about the soil to be tested, a raw soil drilling pressure curve is plotted based on the raw soil drilling pressure data, and the calibration curve is compared with the raw soil drilling pressure curve to determine a first fluctuation factor according to the similarity between the two curves.

In this embodiment, soil physical properties that significantly affect the pressure reading are determined, such as soil humidity, compactness and density. Soil drilling test is conducted on multiple sites, and pressure data is recorded. Meanwhile, soil samples are acquired from each test site, and soil humidity, density and compactness are measured in a laboratory. These soil properties are integrated into a composite index, and the relationship between the composite index and the pressure data measured on site is analyzed by means of a calibration curve. The calibration curve is constructed using statistical methods (e.g. regression analysis). Typically, pressure readings are on a vertical axis, and the soil layer depth is on a horizontal axis, to construct a calibration curve within a certain range, which is an area from the minimum value to the maximum value, and the appropriate curve is selected based on the composite index. The first fluctuation factor refers to the fluctuation determined by the difference from the calibration curve for the soil.

In some embodiments of the present application, the calibration curve is selected based on the basic information about the soil to be tested, specifically including the following.

The basic information of the soil to be tested includes humidity, density, and compactness. A composite index is set according to the humidity, the density, and the compactness. Pre-established calibration curves corresponding to different composite indexes and soil drilling pressure are stored in a database, and the calibration curve represents a range of the soil drilling pressure varying with soil depth.

According to an actual composite index of the soil to be tested, a calibration curve corresponding to the same composite index is identified in the database.

In this embodiment, the composite index can be determined through methods such as weighted averaging of the aforementioned properties. According to the actual composite index, the calibration curve corresponding to the same or closest composite index is identified in the database.

In some embodiments of the present application, the calibration curve is compared with the raw soil drilling pressure curve to determine a first fluctuation factor according to the similarity between the two curves, specifically including the following.

The similarity between the two curves is 100% and the first fluctuation factor is 0 in a case that the raw soil drilling pressure curve is entirely within a range of the calibration curve; and otherwise, a portion of the raw soil drilling pressure curve that exceeds the range of the calibration curve is split into a plurality of exceedance curves according to the soil layer depth, an average difference between each of the exceedance curves and a boundary of the calibration curve is calculated, all average differences are integrated to determine the similarity, and one first fluctuation factor is mapped through the similarity.

In this embodiment, if the raw soil drilling pressure curve is entirely within the range of the calibration curve, it indicates that the raw soil drilling pressure curve is in conformity with the calibration curve and there is a minimal fluctuation. If the raw soil drilling pressure curve exceeds the range of the calibration curve, it indicates a significant fluctuation, which needs to be taken into account. The larger the integrated average difference is, the lower the similarity, and accordingly, the larger the first fluctuation factor will be.

Step S103, a performance fluctuation of the soil drilling device is determined according to the real-time parameters of the soil drilling device, a second fluctuation factor is determined according to the performance fluctuation of the soil drilling device, an IQR coefficient is set based on the first fluctuation factor and the second fluctuation factor, and a box plot of the raw soil drilling pressure data is constructed based on the IQR coefficient.

In this embodiment, the performance fluctuation of the soil drilling device may be affected by various operation parameters, and some key operation parameters are shown as follows.

Drilling rate: the drilling rate can affect the cutting and compression behaviors on soil, thereby affecting the acquisition of pressure data. Unstable drilling rate may lead to inconsistent pressure readings.

Torque: torque is the force applied by a rotating drill bit, affecting penetration power of the drill bit and the degree of soil fragmentation. Unstable torque can bring about fluctuations in pressure.

Drilling pressure: drilling pressure refers to the vertical force applied by the drill bit on the soil. Fluctuations in drilling pressure directly impact the acquisition of pressure data.

Vibration: vibrations during the drilling may affect the readings of a pressure sensor, resulting in data fluctuations.

Rotation speed: the stability of rotation speed is crucial for electric or hydraulic soil drills. Changes in rotation speed affect the penetration power of the drill bit and soil stress.

Cooling system: the drill bit and drill machine may overheat during operation for a long time. The performance of the cooling system affects the efficiency and stability of the device.

Stability of power supply: for electric soil drills, the stability of power supply influences the performance of motor, further influencing the drilling rate and torque.

Hydraulic system pressure: for hydraulic soil drills, the stability of hydraulic system pressure affects the performance of hydraulic motor, subsequently influencing the drilling rate and torque.

In this embodiment, the second fluctuation factor represents the performance fluctuation of the soil drilling device, and the IQR coefficient is set according to the first fluctuation factor and the second fluctuation factor. The box plot is employed to describe the abnormal values and normal values of pressure data. Generally speaking, a box plot includes a lower bound, a lower quartile Q1, a median Q2, an upper quartile Q3, and an upper bound. The lower quartile Q1, the median Q2, and the upper quartile Q3 represent the first quartile, the second quartile, and the third quartile, respectively, which are essentially the $25_{th}$, $50_{th}$, and $75_{th}$ percentiles, respectively. The IQR is defined as IQR=Q3−Q1. Conventionally, the lower bound=Q1−

1.5IQR, and the upper bound=Q3+1.5IQR, which are in the premise that the data follows a normal distribution, but generally speaking, it is rarely the case in practice. To ensure the accuracy of the box plot, adjustments are made to the IQR coefficient. Data within the upper and lower bounds are normal, and data outside these bounds are abnormal.

In a box plot, the upper and lower bounds are defined based on IQR, and 1.5IQR is typically used as the criterion for identifying abnormal values. 1.5 is an empirical rule assuming that the data follows a normal distribution, in which, approximately 99.3% of the data falls within the range of Q1−1.5IQR and Q3+1.5IQR. However, affected by the fluctuations in both the soil drilling device and the soil itself, this coefficient needs to be adjusted to better filter out abnormal values. For example, if the performance fluctuation of the device is larger, a more lenient IQR coefficient (such as 1.2IQR or 1.3IQR) can be considered to be used. If the performance fluctuation of the device is smaller, a stricter IQR coefficient (such as 1.5IQR or 1.8IQR) can be considered to be used.

In some embodiments of the present application, a performance fluctuation of the soil drilling device is determined according to the real-time parameters of the soil drilling device, specifically including the following.

The real-time parameters of the soil drilling device are obtained during soil drilling, a parameter change curve for each of the real-time parameters changing over time is constructed, each parameter change curve is split into a plurality of small curves according to the fluctuation degree of each of the real-time parameters, a slope change of each of the small curves is calculated to obtain an average value of overall slope change of the parameter change curve, the real-time parameters are divided into stable parameters and unstable parameters according to the average value of slope change, and standardization processing is performed on the stable parameters and the unstable parameters.

The performance fluctuation of the soil drilling device is determined according to the stable parameters and the unstable parameters.

$$M = \sum_{i=1}^{n1} (\alpha_i Q_i) \ln \left\{ \frac{\sum_{j=0}^{n2} (\beta_j W_j)}{k_1} \right\} - M_0$$

where M represents the performance fluctuation of the soil drilling device, n1 represents the number of types of the stable parameters, $\alpha_i$ represents a performance weight of an $i_{th}$ type of stable parameters, $Q_i$ represents a size of the $i_{th}$ type of stable parameters, n2 represents the number of types of the unstable parameters, $\beta_j$ represents a performance weight of a $j_{th}$ type of unstable parameters, $W_j$ represents a size of the $j_{th}$ type of unstable parameters, $k_1$ represents a first constant, and $M_0$ represents a standard performance fluctuation range of the soil drilling device.

In this embodiment, if the performance fluctuation $$\sum_{i=1}^{n1} (\alpha_i Q_i) \ln \left\{ \frac{\sum_{j=0}^{n2} (\beta_j W_j)}{k_1} \right\}$$

characterized by the stable parameters corrected by the unstable parameters is less than $M_0$, M=0, with ln

9

$$\left\{ \frac{\sum_{j=0}^{n2}(\beta_j W_j)}{k_1} \right\}$$

ranging from 0.89 to 1.21.

In some embodiments of the present application, an IQR coefficient is set based on the first fluctuation factor and the second fluctuation factor, and a box plot of the raw soil drilling pressure data is constructed based on the IQR coefficient, specifically including the following.

$$D = \left[ \left( \gamma_1 \max\{s_1, s_2\} + \gamma_2 \left( \frac{s_1 + s_2}{2} \right) \right) \rightarrow D_1 \right] + D_2 \qquad 15$$

where D represents the IQR coefficient, $\gamma_1$ represents a fluctuation weight of a larger fluctuation factor, $\max\{s_1, s_2\}$ represents a larger one in the first fluctuation factor and the second fluctuation factor, $s_1$ represents the first fluctuation factor, $s_2$ represents the second fluctuation factor, $\gamma 2$ represents a fluctuation weight of an average value of the first fluctuation factor and the second fluctuation factor, $$\left( \gamma_1 \max\{s_1, s_2\} + \gamma_2 \left( \frac{s_1 + s_2}{2} \right) \right) \rightarrow D_1$$

represents an IQR compensation coefficient obtained by jointly mapping the larger fluctuation factor and the average value of the fluctuation factors, and $D_2$ represents an initial IQR coefficient.

Upper and lower bounds in the box plot are determined according to the IQR coefficient, from which the box plot of the raw soil drilling pressure data is constructed.

In this embodiment, the compensation coefficient is determined based on the larger factor and the average value of the two factors, with an initial IQR coefficient being 1.5.

Step S104, a peak soil drilling pressure is determined according to the box plot of the raw soil drilling pressure data, and nitrogen leaching risk is determined according to a depth interval of soil layer where the peak soil drilling pressure is located.

In some embodiments of the present application, a peak soil drilling pressure is determined according to the box plot of the raw soil drilling pressure data, specifically including the following.

Normal soil drilling pressure data is differentiated from abnormal soil drilling pressure data according to the upper and lower bounds in the box plot of the raw soil drilling pressure data, the peak soil drilling pressure is determined in the normal soil drilling pressure data, and the abnormal soil drilling pressure data is removed.

In some embodiments of the present application, nitrogen leaching risk is determined according to a depth interval of soil layer where the peak soil drilling pressure is located, specifically including the following.

Other soil conditions are obtained, including groundwater underflow and soil barriers, and the nitrogen leaching risk is comprehensively determined by combining the groundwater underflow, the soil barriers, and the depth of soil layer, as shown in Table. 1.

10

TABLE 1

| Peak soil layer cm | Ground-water underflow (Yes/No) | Soil barrier | Nitro-gen leaching risk | Recommended technique |
|---|---|---|---|---|
| 0-30 | — | Hardening | Middle | ≥30 cm deep plowing, combined application of organic fertilizer, precision fertilization, straw turnover, and soil amendments |
| | | Sali-nization | Middle | Subsoiling, organic fertilizer, straw turnover, precision fertilization, and soil amendments |
| 30-60 | — | Non | Low | — |
| | | Sali-nization | Middle | Smash-ridging and subsoiling, organic fertilizer, deep burial of straw for returning to the field, precision fertilization, and soil amendments |
| 60-100 | No | Non | Low | — |
| | Yes | Non | High | Increase of monitoring sites, precision fertilization, water-saving irrigation, intercropping of deep-rooted and shallow-rooted crops, and substrate planting to construct a sponge layer, etc. |
| 100-200 | No | Non | Low | — |
| | Yes | Non | High | Increase of monitoring sites, precision fertilization, water-saving irrigation, intercropping of deep-rooted and shallow-rooted crops, and buried pipe drainage and recovery |
| >200 | — | Non | Low | Reduction of monitoring sites |

According to the above technical solutions, soil drilling pressure data is acquired from a plurality of soil layers of different depths on soil to be tested using a soil drilling device, to obtain raw soil drilling pressure data, and real-time parameters of the soil drilling device are monitored; a calibration curve is selected based on the basic information about the soil to be tested, a raw soil drilling pressure curve is plotted based on the raw soil drilling pressure data, and the calibration curve is compared with the raw soil drilling pressure curve to determine a first fluctuation factor according to the similarity between the two curves; a performance fluctuation of the soil drilling device is determined according to the real-time parameters of the soil drilling device, a second fluctuation factor is determined according to the performance fluctuation of the soil drilling device, an IQR coefficient is set based on the first fluctuation factor and the second fluctuation factor, and a box plot of the raw soil drilling pressure data is constructed based on the IQR coefficient; and a peak soil drilling pressure is determined according to the box plot of the raw soil drilling pressure data, and nitrogen leaching risk is determined according to a depth interval of soil layer where the peak soil drilling pressure is located. In the present application, the IQR coefficient is set based on the first fluctuation factor and the second fluctuation factor; the impact of both the soil drilling device and soil conditions on data acquisition is comprehensively considered, and a reasonable IQR coefficient is set to construct the box plot of the pressure data, allowing for the filtering out of abnormal values. This improves the adaptability of data processing and accurately determines peak pressure, ensuring the accuracy of assessing the nitrogen leaching risk in soil.

Through the above description of the implementation, those skilled in the art can clearly appreciate that the present disclosure can be realized by means of hardware, or realized by means of software combined with the necessary general hardware platform. On the basis of this understanding, the technical solutions of the present disclosure may be embodied in the form of a software product, which can be stored in a non-volatile storage medium (such as compact disc read-only memory, USB flash disk and mobile hard disk drive) including a number of instructions for causing a computer device (which may be a personal computer, a server, or a network device, etc.) to implement the method described in the various embodiments of the present disclosure.

Accordingly, the present application also provides a system for assessing nitrogen leaching risk in farmland, as shown in FIG. 2, including:

a soil drilling module, configured to acquire soil drilling pressure data from a plurality of soil layers of different depths on soil to be tested using a soil drilling device, to obtain raw soil drilling pressure data, and monitor real-time parameters of the soil drilling device;

a calibration module, configured to select a calibration curve based on the basic information about the soil to be tested, plot a raw soil drilling pressure curve based on the raw soil drilling pressure data, and compare the calibration curve with the raw soil drilling pressure curve to determine a first fluctuation factor according to the similarity between the two curves;

a construction module, configured to determine a performance fluctuation of the soil drilling device according to the real-time parameters of the soil drilling device, determine a second fluctuation factor according to the performance fluctuation of the soil drilling device, set an IQR coefficient based on the first fluctuation factor and the second fluctuation factor, and construct a box plot of the raw soil drilling pressure data based on the IQR coefficient; and an assessment module, configured to determine a peak soil drilling pressure according to the box plot of the raw soil drilling pressure data, determine nitrogen leaching risk according to a depth interval of soil layer where the peak soil drilling pressure is located, and provide a solution to the risk.

To further state the technical concept of the present disclosure, the technical solutions of the present disclosure are stated in the context of specific application scenarios.

In the present application, based on soil drilling pressure records during sampling at different soil layers (depths) of a site, the data is processed correspondingly to assess nitrogen leaching risk during sampling and provide locally applicable nitrogen leaching prevention and control techniques. The assessment method described in this patent contributes to reducing environmental losses of nitrogen, improving farmland soil, and protecting water resources.

In the prior art, the soil drilling method for in-situ soil collection is conventional for field background investigations, which involves that after air-drying the collected farmland soil and sieving it through a 2 mm sieve, the mechanical composition of soil is measured using a densimeter, and soil texture is determined, which is time-consuming and labor-intensive. If soil texture profiles can be directly obtained during in-situ soil collection, pollution prevention and control, as well as farmland improvement techniques suitable for this plot can be immediately obtained.

The soil monitoring range for vegetable crops is 0-1 m, the soil profile monitoring range for field crops such as wheat and corn is 0-2 m, and the monitoring range for orchards and other gardens can be extended to 3 m.

1. If the peak pressure appears in topsoil of <30 cm, (<100 cm for orchards), it indicates soil hardening in the topsoil. Accordingly, soil improvement is primary while nitrogen leaching risk prevention is secondary. The techniques such as precision fertilization, combined application of organic fertilizers, soil amendments like biochar, straw turnover, and deep plowing can be employed to improve the soil structure, and increase soil permeability and water retention capability.

2. If the peak pressure appears in subsurface soil of 30-60 cm (100-200 cm for orchards), soil improvement is primary while nitrogen leaching risk prevention is secondary. The techniques of subsoiling to break the plow pan, combining with organic fertilizer application, and straw turnover are employed. For salinized soil, subsoiling to break the plow pan can significantly alleviate the harm caused by salinization.

3. If the peak pressure appears in soil layer of 60-100 cm (200-300 cm for orchards), for soil in field and vegetable field, nitrogen leaching prevention techniques are primary by using precision fertilization, water-saving irrigation, combined application of organic fertilizer, straw turnover, and intercropping of deep-rooted and shallow-rooted crops to prevent the deep leaching of nutrients. For orchards, soil improvement is still primary by subsoiling to break the plow pan, promoting root growth downwards, and enhancing crop yield.

4. If the peck pressure appears in soil layer of 100-200 cm (>300 cm for orchards), it indicates a lower nitrogen leaching risk, and accordingly, monitoring sites can be reduced in these layers.

It there are no peaks detected in 0-200 cm of soil layers, it indicates that the soil is sandy, which is prone to nitrogen leaching, and accordingly, monitoring sites are required to be increased, and measures like buried drainage and recovery, and substrate cultivation can be taken.

5. If groundwater appears at 60-200 cm when the soil drill is pulled out, it indicates that there is a high risk of nitrogen leaching into shallow groundwater, which is prone to non-point source pollution. In this area, precise application of nitrogen fertilizers needs to be paid attention to, and controlled-release fertilizers are recommended.

It is to be noted that: the embodiments as described above are merely used for illustrating the technical solutions of the present application, rather than limiting the present application. Although the present application is described in detail by reference to the foregoing embodiments, it is to be understood by those ordinary skilled in the art that the technical solution set forth in each embodiment can still be modified or some technical features can be replaced equivalently, and those modifications or equivalent replacements cannot make the modified technical solution out of the spirit and scope of the technical solution of the present application.

The invention claimed is:

1. A computer-implemented method for assessing nitrogen leaching risk based on farmland soil pressure, comprising the following steps:

instructing a soil drilling device to acquire soil drilling pressure data from a plurality of soil layers of different depths on soil to be tested, to obtain raw soil drilling pressure data, and monitoring real-time parameters of the soil drilling device;

selecting a calibration curve based on basic information about the soil to be tested, plotting a raw soil drilling pressure curve based on the raw soil drilling pressure data, and comparing the calibration curve with the raw soil drilling pressure curve to determine a first fluctuation factor according to a similarity between the calibration curve and the raw soil drilling pressure curve;

determining a performance fluctuation of the soil drilling device according to the real-time parameters of the soil drilling device, determining a second fluctuation factor according to the performance fluctuation of the soil drilling device, setting an interquartile range (IQR) coefficient based on the first fluctuation factor and the second fluctuation factor, and constructing a box plot of the raw soil drilling pressure data based on the IQR coefficient;

determining a peak soil drilling pressure according to the box plot of the raw soil drilling pressure data, and determining nitrogen leaching risk according to a depth interval of soil layer where the peak soil drilling pressure is located;

determining a nitrogen prevention and control plan, and a farmland improvement scheme based on the nitrogen leaching risk; and performing the nitrogen prevention and control plan and the farmland improvement scheme on the soil.

2. The computer-implemented method for assessing nitrogen leaching risk based on farmland soil pressure according to claim 1, wherein the selecting a calibration curve based on the basic information about the soil to be tested comprises:

the basic information of the soil to be tested comprising humidity, density, and compactness, setting a composite index according to the humidity, the density, and the compactness, and storing preset calibration curves corresponding to different composite indexes and soil drilling pressure in a database, the calibration curve representing a range of the soil drilling pressure varying with soil depth; and identifying, according to an actual composite index of the soil to be tested, a calibration curve corresponding to the same composite index in the database.

3. The computer-implemented method for assessing nitrogen leaching risk based on farmland soil pressure according to claim 2, wherein the comparing the calibration curve with the raw soil drilling pressure curve to determine a first fluctuation factor according to the similarity between the two curves comprises:

the similarity between the two curves being 100%, and the first fluctuation factor being 0 in a case that the raw soil drilling pressure curve is entirely within a range of the calibration curve; and otherwise, splitting a portion of the raw soil drilling pressure curve that exceeds the range of the calibration curve into a plurality of exceedance curves according to soil layer depth, calculating an average difference between each of the exceedance curves and a boundary of the calibration curve, integrating all average differences to determine the similarity, and mapping one first fluctuation factor through the similarity.

4. The computer-implemented method for assessing nitrogen leaching risk based on farmland soil pressure according to claim 1, wherein the determining a performance fluctuation of the soil drilling device according to the real-time parameters of the soil drilling device comprises:

obtaining the real-time parameters of the soil drilling device during soil drilling, constructing a parameter change curve for each of the real-time parameters changing over time, splitting each parameter change curve into a plurality of small curves according to the fluctuation degree of each of the real-time parameters, calculating a slope change of each of the small curves, to obtain an average value of overall slope change of the parameter change curve, dividing the real-time parameters into stable parameters and unstable parameters according to the average value of slope change, and performing standardization processing on the stable parameters and the unstable parameters; and determining the performance fluctuation of the soil drilling device according to the stable parameters and the unstable parameters;

$$M = \sum_{i=1}^{n1} (\alpha_i Q_i) \ln \left\{ \frac{\sum_{j=0}^{n2} (\beta_j W_j)}{k_1} \right\} - M_0$$

where M represents the performance fluctuation of the soil drilling device, n1 represents the number of types of the stable parameters, $\alpha_i$ represents a performance weight of an $i_{th}$ type of stable parameters, $Q_i$ represents a size of the $i_{th}$ type of stable parameters, n2 represents the number of types of the unstable parameters, $\beta_j$ represents a performance weight of a $j_{th}$ type of unstable parameters, $W_j$ represents a size of the $j_{th}$ type of unstable parameters, $k_1$ represents a first constant, and $M_0$ represents a standard performance fluctuation range of the soil drilling device.

5. The computer-implemented method for assessing nitrogen leaching risk based on farmland soil pressure according to claim 4, wherein the setting an IQR coefficient based on the first fluctuation factor and the second fluctuation factor, and constructing a box plot of the raw soil drilling pressure data based on the IQR coefficient comprises:

$$D = \left[ \left( \gamma_1 \max\{s_1, s_2\} + \gamma_2 \left( \frac{s_1 + s_2}{2} \right) \right) \rightarrow D_1 \right] + D_2$$

where D represents the IQR coefficient, $\gamma_1$ represents a fluctuation weight of a larger fluctuation factor, $\max\{s_1, s_2\}$ is a larger one in the first fluctuation factor and the second fluctuation factor, $s_1$ represents the first fluctuation factor, $s_2$ represents the second fluctuation factor, $\gamma_2$ represents a fluctuation weight of an average value of the first fluctuation factor and the second fluctuation factor, $$\left( \gamma_1 \max\{s_1, s_2\} + \gamma_2 \left( \frac{s_1 + s_2}{2} \right) \right) \rightarrow D_1$$

represents an IQR compensation coefficient obtained by jointly mapping the larger fluctuation factor and the average value of the fluctuation factors, and $D_2$ represents an initial IQR coefficient; and determining upper and lower bounds in the box plot according to the IQR coefficient, from which the box plot of the raw soil drilling pressure data is constructed.

6. The computer-implemented method for assessing nitrogen leaching risk based on farmland soil pressure according to claim 5, wherein the determining a peak soil drilling pressure according to the box plot of the raw soil drilling pressure data comprises:

US 12,601,730 B2

15 / 16 differentiating normal soil drilling pressure data from abnormal soil drilling pressure data according to the upper and lower bounds in the box plot of the raw soil drilling pressure data, determining the peak soil drilling pressure in the normal soil drilling pressure data, and removing the abnormal soil drilling pressure data.

7. The computer-implemented method for assessing nitrogen leaching risk based on farmland soil pressure according to claim 1, wherein the determining nitrogen leaching risk according to a depth interval of soil layer where the peak soil drilling pressure is located comprises:

obtaining other soil conditions, including groundwater underflow and soil barriers, and comprehensively determining the nitrogen leaching risk by combining the groundwater underflow, the soil barriers, and the depth interval of soil layer.

* * * * *